US011410753B2

(12) United States Patent
Khatri et al.

(10) Patent No.: US 11,410,753 B2
(45) Date of Patent: Aug. 9, 2022

(54) SYSTEM AND METHODS OF CAPTURING MEDICAL IMAGING DATA USING A MOBILE DEVICE

(71) Applicant: Hyland Switzerland Sarl, Geneva (CH)

(72) Inventors: Abdul Rahim Khatri, San Ramon, CA (US); Jacob Michael Hargus, Brentwood, CA (US)

(73) Assignee: Hyland Switzerland SARL, Geneva (CH)

(*) Notice: Subject to any disclaimer, the term of this patent is extended or adjusted under 35 U.S.C. 154(b) by 730 days.

(21) Appl. No.: 15/395,423

(22) Filed: Dec. 30, 2016

(65) Prior Publication Data
US 2018/0189447 A1 Jul. 5, 2018

(51) Int. Cl.
| | |
|---|---|
| *G16H 10/60* | (2018.01) |
| *H04N 7/18* | (2006.01) |
| *G16H 40/63* | (2018.01) |
| *G16H 30/40* | (2018.01) |
| *G16H 30/20* | (2018.01) |

(Continued)

(52) U.S. Cl.
CPC .......... *G16H 10/60* (2018.01); *G06K 7/1099* (2013.01); *G16H 30/20* (2018.01); *G16H 30/40* (2018.01); *G16H 40/63* (2018.01); *G16H 50/20* (2018.01); *H04N 7/185* (2013.01); *G06F 21/6245* (2013.01); *H04L 63/083* (2013.01)

(58) Field of Classification Search
CPC .... H04L 63/083; H04N 7/185; G06K 7/1099; G16H 10/60

USPC .......................................................... 705/2, 3
See application file for complete search history.

(56) References Cited

U.S. PATENT DOCUMENTS 9,411,823 B1 * 8/2016 Rice ........................ G06F 19/321
2003/0013959 A1 * 1/2003 Grunwald ............... A61B 8/468
600/437

(Continued)

OTHER PUBLICATIONS

Adam Landman et al., A Mobile App for Securely Capturing and Transferring Clinical Images to the Electronic Health Record: Description and Preliminary Usability Study, JMIR Mhealth Uhealth. Jan.-Mar. 2015; 3(1): e1. Published online Jan. 2, 2015. doi: 10.2196/mhealth.3481 (Year: 2015).*

(Continued)

*Primary Examiner* — Joshua B Blanchette
(74) *Attorney, Agent, or Firm* — BakerHostetler

(57) ABSTRACT

Methods for associating medical images to a patient using a mobile image-capturing device and transmitting the medical images to a storage location are disclosed. One example method includes accessing by a user identifying information associated with a patient through an electronic health record (EHR) application installed in the mobile device, launching a second application on the mobile device from the EHR application, and upon the launching of the application from the EHR application, transmitting the patient identifying information accessed by the user from the EHR application to the second application. The second application may then retrieve one or more medical images stored in the mobile device, associate the one or more retrieved medical images with the patient using the identifying information, and transmit the one or more retrieved medical images with the associated patient identifying information from the mobile device to a storage location.

16 Claims, 6 Drawing Sheets

(51) Int. Cl.
*H04L 9/40* (2022.01)
*G06K 7/10* (2006.01)
*G16H 50/20* (2018.01)
*G06F 21/62* (2013.01)

(56) References Cited

U.S. PATENT DOCUMENTS

| | | | |
|---|---|---|---|
| 2006/0242148 A1* | 10/2006 | Rothpearl | G16H 30/20 |
| 2008/0021741 A1* | 1/2008 | Holla | G16H 10/60 |
| | | | 705/3 |
| 2008/0249801 A1* | 10/2008 | Zaleski | A61B 5/0006 |
| | | | 705/2 |
| 2013/0177222 A1* | 7/2013 | Tridandapani | A61B 5/117 |
| | | | 382/128 |
| 2014/0142984 A1* | 5/2014 | Wright | G06F 19/321 |
| | | | 705/3 |
| 2014/0257047 A1* | 9/2014 | Sillay | A61B 5/11 |
| | | | 600/301 |
| 2015/0154371 A1* | 6/2015 | Wald | G16H 30/40 |
| | | | 705/2 |
| 2018/0189446 A1 | 7/2018 | Khatri et al. | |
| 2018/0189447 A1 | 7/2018 | Khatri et al. | |

OTHER PUBLICATIONS

Khatri et al., U.S. Appl. No. 15/395,327, filed Dec. 30, 2016.

* cited by examiner

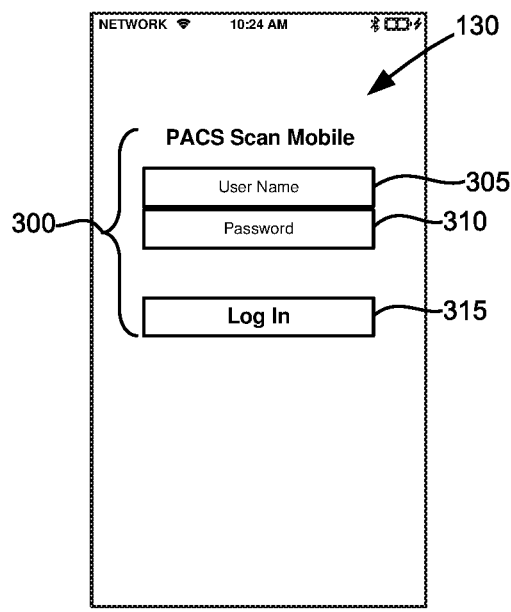
FIG. 3
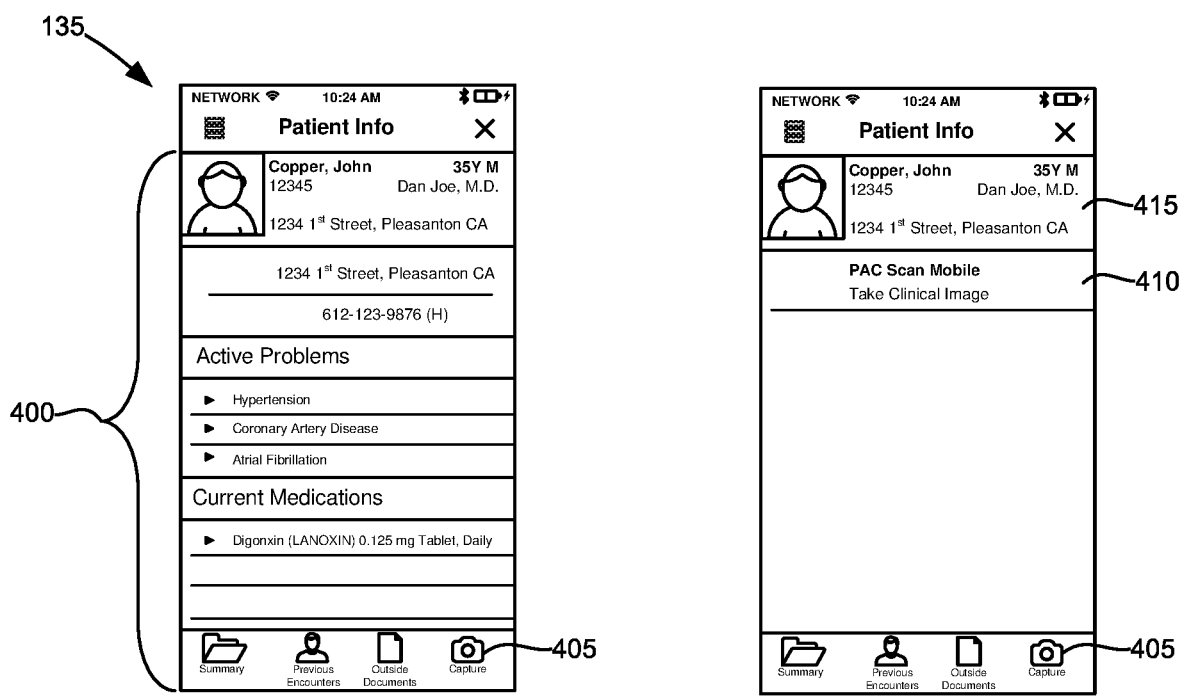
FIG. 4A          FIG. 4B

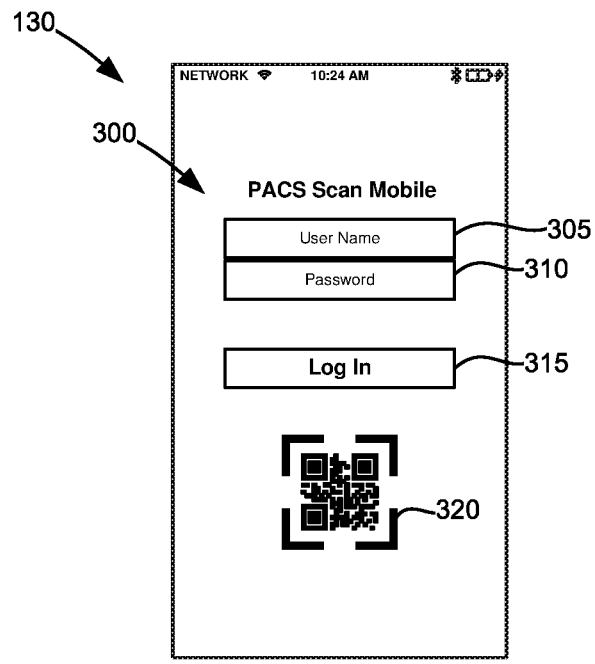
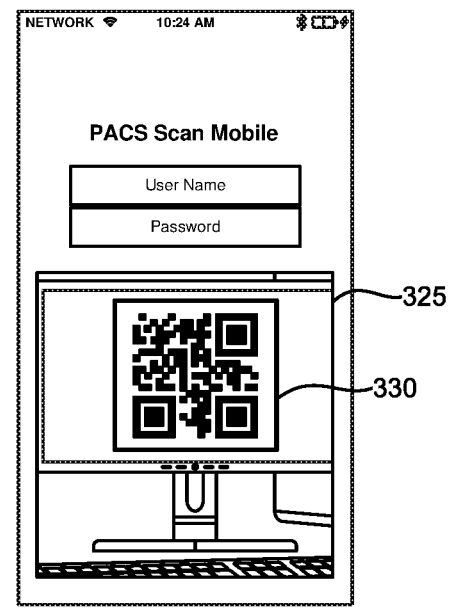
FIG. 5A  FIG. 5B
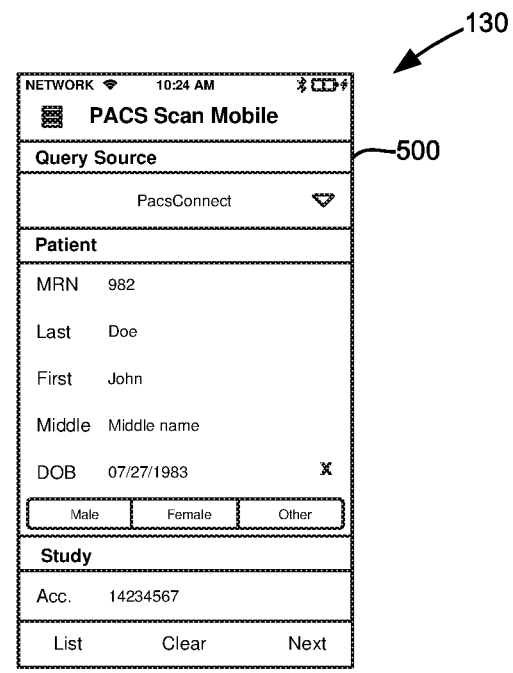
FIG. 5C  FIG. 5D

SYSTEM AND METHODS OF CAPTURING MEDICAL IMAGING DATA USING A MOBILE DEVICE

CROSS REFERENCES TO RELATED APPLICATIONS

The present application is related to U.S. patent application Ser. No. 15/395,327, entitled "System and Methods of Capturing Medical Imaging Data Using a Mobile Device," filed on Dec. 30, 2016 and assigned to the assignee of the present application, the contents of which is hereby incorporated by reference herein in its entirety.

STATEMENT REGARDING FEDERALLY SPONSORED RESEARCH OR DEVELOPMENT

None.

REFERENCE TO SEQUENTIAL LISTING, ETC

None.

BACKGROUND

1. Technical Field

The present invention relates generally to a system and methods of capturing medical data. More specifically, it relates to a system and methods of capturing medical imaging data and associating the captured imaging data to a patient using a mobile device.

2. Description of the Related Art

In a medical imaging environment, different devices are used to capture image and/or video data which may be referred to herein as medical imaging data. Medical imaging typically incorporates radiology and cardiology which utilize different imaging technologies to capture medical imaging data. Some of these technologies include magnetic resonance imaging, x-ray radiography, endoscopy, and medical ultrasonography or ultrasound. However, there is an alternative way to capture medical imaging data that may not be related to radiology or cardiology that may be relevant to other fields of medicine such as, for example, in the field of dermatology. In dermatology, alternative image capturing techniques may be performed to capture important medical imaging data that do not necessarily fit in the regular radiology paradigm.

One of these techniques is to use a mobile imaging device such as, for example, a smart phone to capture medical images. While smart phones may be conveniently used to capture medical imaging data, there is still a need for an efficient and secure system and methods to capture data using the mobile device, organize the captured data, and then store the data on vendor neutral archives (VNAs), picture and archiving communication systems (PACS), and other healthcare systems.

With the availability of other types of imaging devices that can be used to capture medical imaging data outside the typical radiology imaging department, there is a need to capture medical imaging data, associate the captured medical imaging data with patient data, and then allow the users to store the data on VNAs, PACS, and other healthcare systems. There is a need for a solution that will allow users to integrate electronic healthcare record (EHR) systems to PACS to securely share and store the patient data along with medical imaging data captured from alternative imaging modalities such as the mobile devices.

SUMMARY

System and methods for capturing medical imaging data associated with a patient using a mobile image-capturing device are disclosed. One example method of capturing medical images using a mobile device includes receiving, from a user, a request for access to a patient identifying information through an electronic health record application installed in the mobile image-capturing device. The electronic health record application may retrieve patient information such as patient demographics from an electronic health record server communicatively connected to the mobile device. The user may launch a scan application installed in the mobile device from the electronic health record application. The user may click a function in the electronic health record application such as a link or a uniform resource locator (URL) schema that, upon selection, triggers the launch of the scan application from the electronic health record application. Upon the launching of the scan application, the scan application may be provided with the patient information that may have been accessed by the user from the electronic health record application prior to triggering the launch of the scan application. The electronic health record application may provide the patient information via a parameter of the URL schema that was used to launch the scan application.

The scan application may then be used to retrieve or import one or more medical images stored in the mobile image-capturing device to the scan application. The scan application may associate the one or more captured medical images with the patient identifying information and wirelessly transmit the one or more captured medical images with the associated patient identifying information from the mobile image-capturing device to a storage location. In one alternative example embodiment, the user may modify the patient information prior to transmitting the captured medical images with the associated patient identifying information to the storage location. In another alternative example embodiment, the user may select a destination storage location to which the captured medical images and patient identifying information will be sent.

From the foregoing disclosure and the following detailed description of various example embodiments, it will be apparent to those skilled in the art that the present disclosure provides a significant advance in the art of methods for capturing medical images associated with a patient using a mobile image-capturing device. Additional features and advantages of various example embodiments will be better understood in view of the detailed description provided below.

BRIEF DESCRIPTION OF THE DRAWINGS

The above-mentioned and other features and advantages of the present disclosure, and the manner of attaining them, will become more apparent and will be better understood by reference to the following description of example embodiments taken in conjunction with the accompanying drawings. Like reference numerals are used to indicate the same element throughout the specification.

FIG. 3 shows an example login screen for a PACS mobile scan application.

FIGS. 4A-4B illustrate an alternative example embodiment of launching a mobile scan application from another application in a mobile imaging device.

FIGS. 5A-5D illustrate an alternative example embodiment of launching a mobile scan application using a QR code.

DETAILED DESCRIPTION OF THE DRAWINGS

Figure 1:
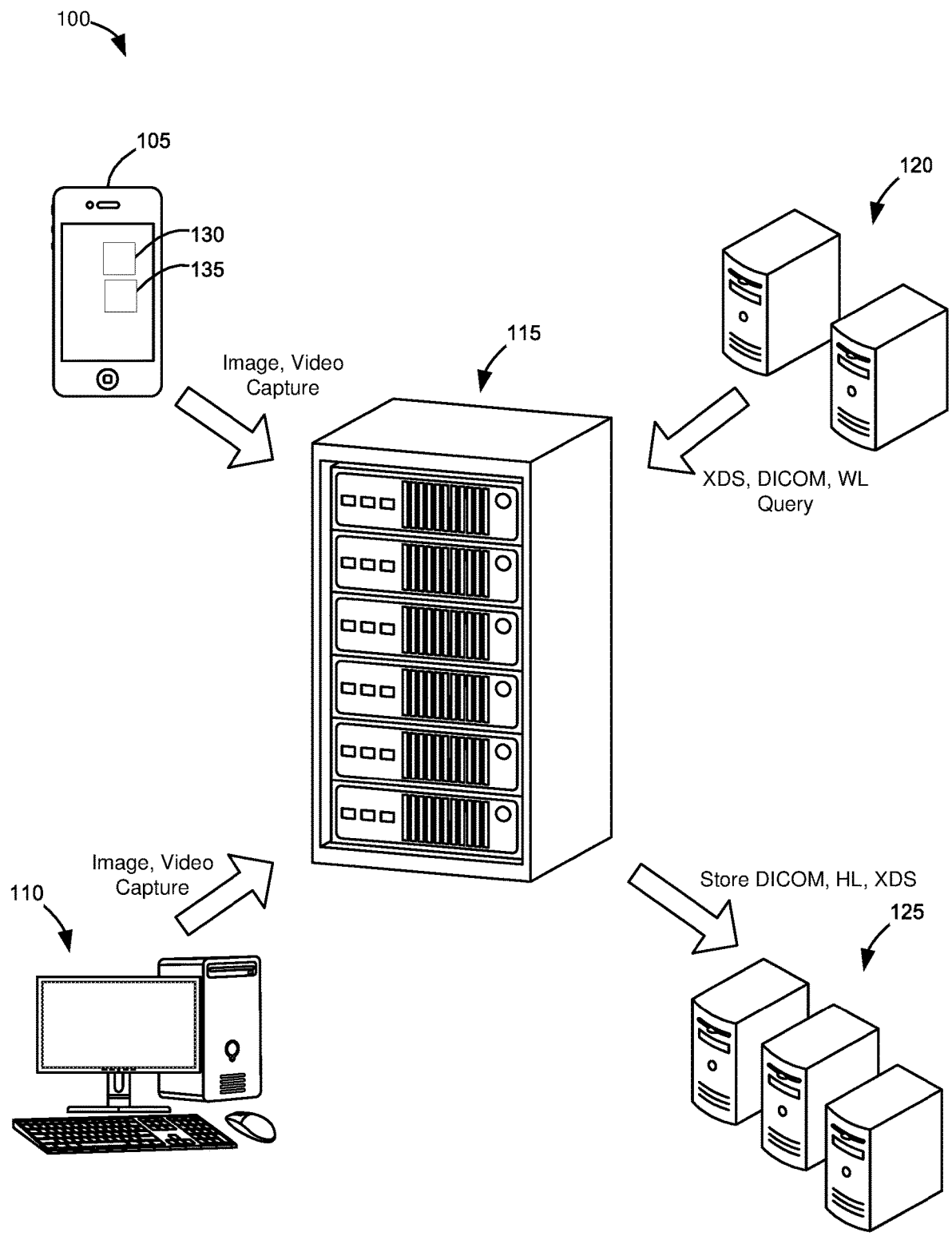
FIG. 1 shows an example system for capturing medical imaging content.

It is to be understood that the disclosure is not limited to the details of construction and the arrangement of components set forth in the following description or illustrated in the drawings. The disclosure is capable of other example embodiments and of being practiced or of being carried out in various ways. For example, other example embodiments may incorporate structural, chronological, process, and other changes. Examples merely typify possible variations. Individual components and functions are optional unless explicitly required, and the sequence of operations may vary. Portions and features of some example embodiments may be included in or substituted for those of others. The scope of the disclosure encompasses the appended claims and all available equivalents. The following description is, therefore, not to be taken in a limited sense, and the scope of the present disclosure is defined by the appended claims.

Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Further, the use of the terms "a" and "an" herein do not denote a limitation of quantity but rather denote the presence of at least one of the referenced item.

In addition, it should be understood that example embodiments of the disclosure include both hardware and electronic components or modules that, for purposes of discussion, may be illustrated and described as if the majority of the components were implemented solely in hardware.

It will be further understood that each block of the diagrams, and combinations of blocks in the diagrams, respectively, may be implemented by computer program instructions. These computer program instructions may be loaded onto a general purpose computer, special purpose computer, or other programmable data processing apparatus to produce a machine, such that the instructions which execute on the computer or other programmable data processing apparatus may create means for implementing the functionality of each block or combinations of blocks in the diagrams discussed in detail in the description below.

These computer program instructions may also be stored in a non-transitory computer-readable medium that may direct a computer or other programmable data processing apparatus to function in a particular manner, such that the instructions stored in the computer-readable medium may produce an article of manufacture, including an instruction means that implements the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus implement the functions specified in the block or blocks.

Accordingly, blocks of the diagrams support combinations of means for performing the specified functions, combinations of steps for performing the specified functions and program instruction means for performing the specified functions. It will also be understood that each block of the diagrams, and combinations of blocks in the diagrams, can be implemented by special purpose hardware-based computer systems that perform the specified functions or steps or combinations of special purpose hardware and computer instructions.

Disclosed are a system and methods for capturing medical image data and patient demographic data and allowing the users to store data on vendor neutral archives (VNAs), picture archiving and communication system (PACS), and other healthcare systems. In an alternative example embodiment, the user may use an existing EHR system to retrieve patient demographic data, capture the medical image data using an image-capturing device, and store the captured medical image data and the patient demographic data on at least one of VNAs, PACS, and other healthcare systems.

In one example embodiment of the present disclosure, the method may include using an application installed in a mobile device that physicians and authorized staff may use to capture content outside the typical hospital imaging environments. The user may use a built-in image-capturing functionality in the mobile device to capture image and/or video content relating to a patient and attach the content to new or existing patient studies. The captured medical images may be associated with patient demographic data which may be entered by the user, or may be retrieved from an EHR system.

When the user is done capturing, the user may edit the images and/or videos along with the patient demographic data before sending the content to a selected source for storage. In one alternative example embodiment, the user may send an HL7 message including the content to an HL7 device.

For purposes of the present disclosure, it will be appreciated that content may refer to files such as, for example, image files, audio files, video files, and/or documents, among others. Content may also refer to information that provides value for an end-user or content consumer in one or more specific contexts. Content may be shared via one or more media such as, for example, computing devices in a network.

In an example embodiment, content may refer to computerized medical records, or electronic medical records (EMRs), created in a health organization, or any organization that delivers patient care such as, for example, a physician's office, a hospital, or ambulatory environments. EMRs may include orders for drug prescriptions, orders for tests, patient admission information, imaging test results, laboratory results, and/or clinical progress information, among others.

Content may also refer to an electronic health record (EHR) which may be a digital content capable of being distributed, accessed and/or managed across various health care settings. EHRs may include various types of information such as, for example, medical history, demographics, immunization status, radiology images, medical allergies, personal states (e.g., age, weight, etc.), vital signs and/or billing information, among others. EHR and EMR may also be referred to as an electronic patient record (EPR). The terms EHR, EPR, EMR, document, medical imaging data, content and object may be used interchangeably for illustrative purposes throughout the present disclosure.

In another example embodiment, content may also refer to Digital Imaging and Communications in Medicine (DICOM) images. DICOM is a standard or specification for transmitting, storing, printing and handling information in medical imaging. Medical imaging, as will be known in the art, may refer to a process and/or technique used to generate images of the human body, or parts or functions thereof, for medical and/or clinical purposes such as, for example, to diagnose, reveal or examine a disease. The standard set by DICOM may facilitate interoperability of various medical imaging equipment across a domain of health enterprises by specifying and/or defining data structures, workflow, data dictionary, compression and workflow, among other things, for use in generating, transmitting and accessing the images and related information stored on the images. DICOM content may refer to medical images following the file format definition and network transmission protocol as defined by DICOM. DICOM content may include a range of biological imaging results and may include images generated through radiology and other radiological sciences, nuclear medicine, thermography, microscopy and/or medical photography, among many others. DICOM content may be referred to hereinafter as images following the DICOM standard, and non-DICOM content for other forms and types of content, as will be known in the art.

Content may be generated and maintained in association with an institution such as, for example, an integrated delivery network, hospital, physician's office or clinic, to provide patients, health care providers, insurers and/or payors access to records of a patient across a number of facilities. Sharing of content may be performed using network-connected enterprise-wide information systems, and other similar information exchanges or networks, as will be known in the art. The terms patient data, patient demographics and patient metadata may be used interchangeably for illustrative purposes throughout the present disclosure.

FIG. 1 shows an example system 100 for capturing medical imaging content that includes a mobile imaging device 105, a client device 110, a core server 115, an electronic health records (EHR) server 120 and a storage server 125. Mobile imaging device 105 may include installed applications such as a mobile scan application 130 and an EHR application 135. In one example embodiment, system 100 may be a picture archiving and communication system (PACS) which includes a secured network for use in transmission of patient information between the components included in system 100.

Mobile imaging device 105 and client device 110 may be content sources from which the media content may be received. Users may utilize at least one of the mobile imaging device 105 and client device 110 to create and submit content having associated metadata for storage in storage server 125.

Mobile imaging device 105 may be a mobile computing device such as, for example, a smart phone, a tablet computer and other similar computing devices as will be known in the art. Mobile imaging device 105 may be installed with an application such as mobile scan application 130 that allows user to capture images and videos using a built-in camera. Mobile scan application 130 may query and retrieve patient demographics from multiple sources, such as EHR server 120, and interface with another installed application in mobile imaging device 110, such as an EHR application 135, in order to access records from EHR server 120.

Using mobile scan application 130, a user may capture clinical images and/or video, attach the captured content to patient studies, and submit the content along with the patient information to storage systems such as storage server 125. Mobile scan application 130 may be used to edit the patient demographics and/or the captured media before storing the media to storage server 125. Other functions of mobile scan application 130 may include management of mobile device configuration and user access from a web console, creation of department-specific configurations, creation of DICOM and Worklist queries, sending of HL7 messages, and/or viewing of DICOM trace data, server logs and audit logs. Mobile scan application 130 may be configured for departmental use at one or more medical environments, such as hospitals, to capture media content using smart devices and submit that content to storage systems (e.g., PACS, VNA, RIS/HIS) using DICOM, HL7 and/or XDS protocols. Mobile scan application 130 may be configured to work seamlessly with a wide variety of storage systems.

Client device 110 may be a computing device that sends content to core server 105. Content that may be sent by client device 110 may include captured images and/or videos, as well as imaging content. In one example embodiment, client device 110 may be other imaging content sources such as, for example, medical imaging equipment like MRI, X-Ray, ultrasound machines, mammography, CT scanners or many other content sources. Client device 110 may also be a computing device used by organizations such as, for example, a physician's office or a hospital that delivers care.

Core server 115 may be a computing device providing a distributed solution for receiving media content through and from various types of client devices such as, mobile imaging device 105 and client device 110, and route the media content to one or more storage servers 125. Core server 115 may be a desktop server that supports the functionalities of mobile imaging device 105 and, more specifically, the mobile scan application 130 installed in mobile imaging device 105. Core sever 115 may include features that control the flow of data between the different devices in system 100. For example, core server 115 may be used by authorized staff at a healthcare facility to process and store media from various mobile and client devices and send the media to a PACS archive such as, for example, storage server 125. Core server 115 may also allow the user of mobile scan application 130 to send media to one or more XDS destinations. In some example aspects, core server 115 may be a unified platform used in performing various functions including, but not limited to, job management; receiving media; transforming media to other formats such as DICOM, etc.; auditing and event logging, forwarding data, files and/or other information to destinations; and/or any other common or shared function required by multiple products. In one example embodiment, core server 115 may be a PACS scan server that stores and processes data generated from various products and processes.

In one example embodiment, core server 115 may support multiple clients and/or devices simultaneously. Such multiple clients and devices may or may not be mobile devices. Core server 115 may also receive media from a mobile client and send the media to one or more destinations, including but not limited to HL7 reports. Audit and event logging may be supported by core server 115 and is viewable via a web client. Service configuration via the web client may also be available using core server 115. In another example embodiment, core server 115 may allow the user to provision a mobile device as a client using a QR code. Core server 115 may also allow the user to login using other means such as fingerprints.

EHR server 120 may be a database server that stores patient-related data such as electronic health records that are accessed by EHR applications and services such as EHR application 135 installed in mobile device 105. EHR server 120 may be used to retrieve patient demographics upon request by a user through mobile scan application 130. Storage server 125 may be a database server that stores medical content such as medical images and videos captured using mobile imaging device 105 along with patient demographic data. In one example embodiment, storage server 125 may receive data from core server 115. Storage server 125 may be a storage system such as, for example, PACS, VNA, RIS/HIS, that mobile scan application 130 may submit content to using DICOM, HL7 and/or XDS protocols.

Figure 2:
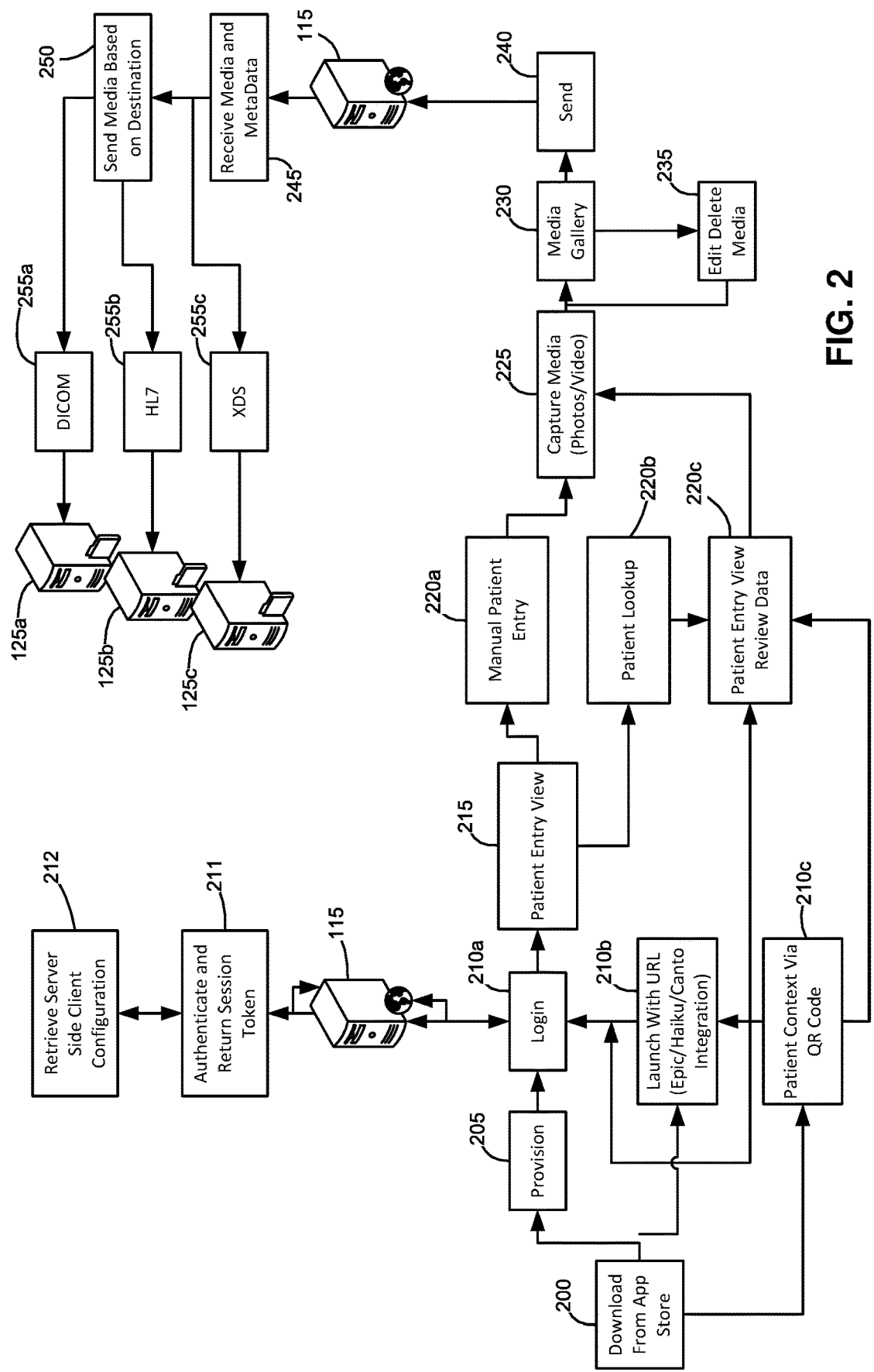
FIG. 2 shows an example method of providing users a means to capture medical imaging data, associate the captured medical imaging data with patient demographic data, and then store the data on VNAs, PACS, and other healthcare systems.

FIG. 2 shows an example method of allowing users to capture medical imaging data, associate the captured medical imaging data with patient demographic data, and then store the data on VNAs, PACS, and other healthcare systems. The method may be performed using the components illustrated in system 100.

At block 200, mobile scan application 130 may be downloaded from an application server such as, for example, an application store. Mobile scan application 130 may be downloaded using mobile imaging device 105 and installed in mobile imaging device 105 for use by the user. Other means for acquiring and installing mobile scan application 130 such as, for example, copying the application to a memory of mobile imaging device 105, will be known in the art.

At block 205, mobile scan application 130 may be provisioned in mobile imaging device 105. At block 210*a*, the user may log in to mobile scan application 130. In one example embodiment, only authorized users may be allowed to log in to mobile scan application 130. The user may start or execute mobile scan application 130, log into the application, and receive application configuration data that may be specific to the user that has logged into mobile scan application 130. In one example embodiment, the user may start mobile scan application 130 and log in to the application by entering user credentials to identify the user attempting to log in, and mobile scan application 130 then attempts to connect to core server 115. The user credentials may include a URL, a username and/or a password.

FIG. 3 shows an example login screen 300 for mobile scan application 130. Login screen 300 may include text areas 305 and 310 where the user may input his or her credentials such as the user name and the password, and a login button 315 for use in logging in the user having the credentials into mobile scan application 130.

Referring back to FIG. 2, at block 210*b*, the user may alternatively login to mobile scan application 130 by launching mobile scan application 130 from another application installed in mobile imaging device 105. The other application may be EHR application 135 that has been integrated with mobile scan application 130. The user may trigger the launch from an external source, and the source may launch mobile scan application 130 using a URL scheme of mobile scan application 130. This alternative example embodiment may be a parameter launch wherein an external source such as a web browser or another application such as EHR application 135, passes configuration and/or patient data to core server 115 on launch in order for mobile scan application 130 to be pre-configured with data as specified from the application which was used to launch mobile scan application 130 such as, for example, EHR application 135. In one example embodiment, the configuration data passed from EHR application 135 to core server 115 on launch may be data that has been set by the user to be used in configuring mobile scan application 130 such as, for example, configuring how an interface of mobile scan application 130 looks, or the specific context with which mobile scan application 130 should be launched. In another example embodiment, EHR application 135 may pass patient data to mobile scan application 130 such that mobile scan application 130 may be provided with patient data to be associated with images to be captured.

FIGS. 4A-4B illustrate an alternative example embodiment of launching mobile scan application 130 from another application in mobile imaging device 105. In this example embodiment, the user may select a function embedded in EHR application 135 to launch mobile scan application 130.

At FIG. 4A, a patient demographic data page 400 may be accessed by the user using example EHR application 135. If the user wishes to capture medical imaging data to be associated to that particular patient, the user may select a Capture function 405 embedded in the patient page of the EHR application 135. Capture function 405 may be a feature in example EHR application 135 that integrates mobile scan application 130 and EHR application 135 such that the user may be given access to capture medical imaging data for a particular patient while viewing details regarding the patient in the patient demographic data page 400 using EHR application 135. Capture function 405 may include a URL scheme of mobile scan application 130 and configuration and/or patient data for use in associating the captured content with the patient from patient demographic data page 400.

In FIG. 4B, upon selecting the Capture function 405, the user may be presented with a link 410 to mobile scan application 130 which, upon selection by the user will lead to example login page 300 of mobile scan application 130. In one example embodiment, the user may need to manually input credentials on login screen 300 of mobile scan application 130. In another example embodiment, the user logged into EHR application 135 may be authorized to use the credentials from EHR application 135 to log into mobile scan application 130 such that upon the user selecting Capture function 405, the user will then be automatically logged into mobile scan application 130 without having the need to manually input the user credentials on login page 300.

When the user selects Capture function 405, EHR application 135 may parse the parameters included in Capture function 405 (e.g., URL scheme, configuration and/or patient data), and if configuration data is present, the data may be set in mobile scan application 130 immediately upon the user accessing mobile scan application 130 via EHR application 135. If configuration data is included in the parameters, the user may be notified that the configuration of mobile scan application 130 has been updated.

If patient data is included in the parameters such as, for example, when the user clicked Capture function 405 while accessing an associated patient demographic 415, the patient data may be checked to verify if it contains at least a last name or a medical record number (MRN) of the patient. If patient data is present along with valid login information, mobile scan application 130 may log the user in with the provided credentials and then display the patient context as specified in the parameters. In one example embodiment, the patient context may be displayed in read-only format.

Referring back to FIG. 2, at block 210c, the user may alternatively login to mobile scan application 130 using an encrypted code such as, for example, a QR code. Mobile scan application 130 may allow the user to provision his device from a QR code provided to the user. In one example embodiment, the QR code may be found in an administrator console.

FIGS. 5A-5D illustrate an alternative example embodiment of launching mobile scan application 130 using a QR code. In FIG. 5A, the user may open mobile scan application 130 and press QR button 320 found on the login page 300 of mobile scan application 130. Upon the user selecting QR button 320, mobile imaging device 105 will open an image-capturing function such as a mobile camera interface 325 that enables the user to aim the camera at a QR code 330 in order to capture the QR code 330 (at FIG. 5B). Once the camera detects the QR code, the camera will dismiss and the service, such as core server 115, may decrypt and then authenticate the captured QR code 330 in order to log in the user to mobile scan application 130 (at FIG. 5C).

Upon successful authentication, the user will be logged into mobile scan application 130, and settings such as the server address and SSL settings that are associated with the captured QR code 330 will be automatically updated by mobile scan application 130. In one example embodiment, QR code 330 may be associated with a patient context which, when used to log in to mobile scan application 130, will redirect the application to open to a page containing the specified patient context as shown in an example patient context page 500 in FIG. 5D. It will be understood that the captured QR code 330 may be encrypted with authorized user credentials and/or patient information that may be used by the user to log in to mobile scan application 130, and/or retrieve and display patient information upon logging in.

When the user attempts to log in to mobile scan application 130 using any of the methods discussed above, the service such as, for example, core server 115, may validate user access and authenticate and return session token for the user's login session to mobile scan application 130 (at block 211 of FIG. 2). If successful, the service may retrieve server-side client configuration (at block 212), and may then return application configuration information. Mobile scan application 130 may then be configured based upon the returned options or information. Application configuration information may include data such as a healthcare department associated with the user and/or the mobile scan application 130, lookups, destinations for storing data generated in mobile scan application 130, and/or default modality, among others. If the user is determined to be authenticated or authorized, the user may be allowed to lookup or create patient data and capture media content to be associated with the patient data. If the user is determined to be unauthorized or authentication fails, a notification may be displayed in an interface of mobile imaging device 105 informing that the user must be successfully logged into the application to continue.

At block 215, upon the user successfully logging into mobile scan application 130, a default page of mobile scan application 130 may be displayed such as, for example, a patient entry view. A default state of the patient entry view may be blank.

Figure 6A:
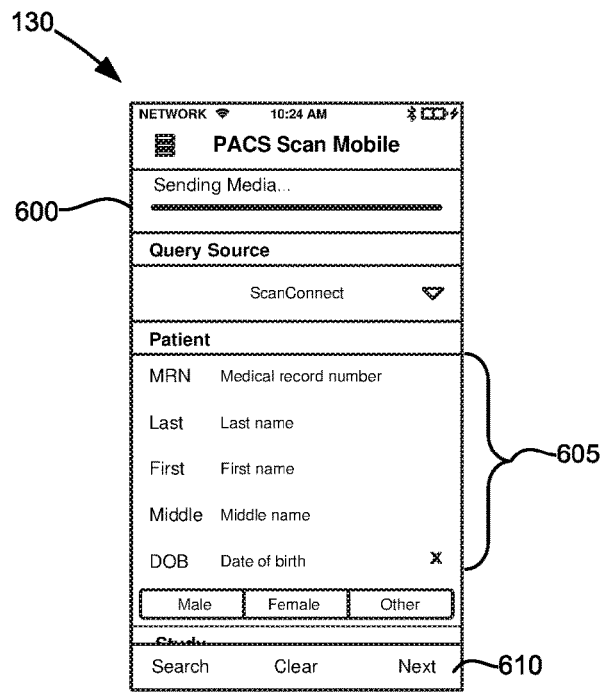
FIG. 6A shows an example blank patient entry view of mobile scan application.
Figure 6B:
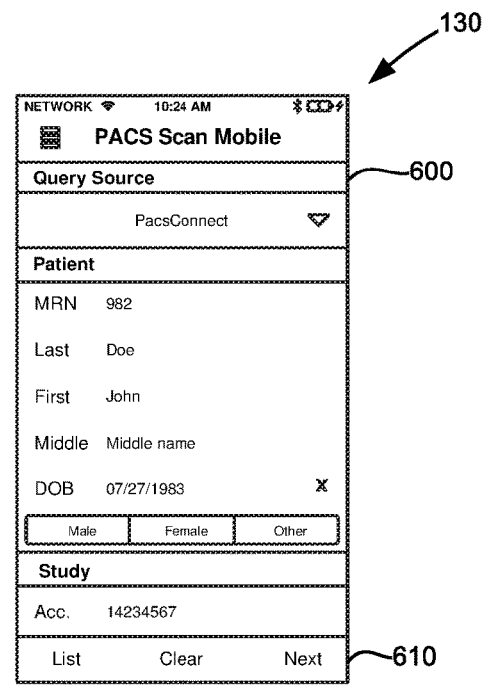
FIG. 6B shows an example blank patient entry view of mobile scan application.

FIG. 6A shows an example blank patient entry view 600 of mobile scan application 130. Patient entry view 600 may include fields that refer to pertinent patient information 605 such as, for example, a medical record number (MRN), last name, first name, middle name, gender, and/or date of birth, among others. Other details such as study DICOM metadata and/or file meta information may also be available in the patient entry view such as, for example, study UID, study date, etc. FIG. 6B shows an example patient entry view having the example fields completed or filled in.

The user may create and/or retrieve patient demographics using mobile scan application 130. In one example embodiment, the user may manually enter the details in the patient entry view 600 (at block 220a of FIG. 2). Manually entering patient data may be performed by typing the details into the corresponding fields, as will be known in the art.

In another example embodiment, at block 220b, the user may perform a patient lookup to search for and retrieve patient information from a database that contains patient information such as, for example, EHR server 120. Mobile scan application 130 may include a function that integrates EHR server 120 which would allow the user to search for patient information using mobile scan application 130. Mobile scan application 130 may query a web service for matching patient information and retrieve a specific patient using a lookup screen (not shown) in mobile scan application 130. The user may enter any of available patient information such as MRN, last name, first name, and/or accession number, hit a lookup button and a table of matching results from the EHR server 120 will be presented to the user.

Figure 7:
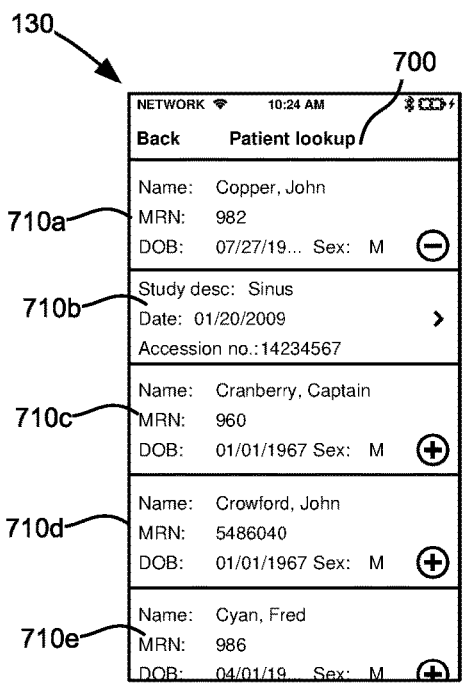
FIG. 7 shows an example table of matching results that displays a list of results from a lookup performed by the user.

FIG. 7 shows an example table of matching results 700 that displays a list of results from a lookup performed by the user. In this example, patient results 710a, 710b, 710c, 710d and 710e are returned after the user has entered C in the last name text field of the lookup screen (not shown). The user may then select a desired patient and/or study from the results shown in table 700, and mobile scan application 130 may display an editable patient entry view 600 which allows the user the review the retrieved data (at block 220c of FIG. 2). In one example embodiment, mobile scan application 130 may query multiple sources for the patient demographics. A query source may be a DICOM worklist server, archive, or other source that can respond to patient queries. In one example embodiment, to be able to query patient studies using mobile scan application 130, the user may configure at least one query source.

The user may be allowed to edit the patient information during a session in mobile scan application 130. The user may edit the patient information while captured media content has been saved locally. Once the user hits a send button, the edited patient metadata and the captured media may be sent to at least one of core server 115 and EHR server 120. Core server 115 may process the data and forward DICOM files to a selected destination such as, for example, storage server 125. In one alternative example embodiment, the metadata may be sent to a destination server which may be at least one of core server 115 and EHR server 120. The destination server may return a value such as, for example, a URL back to mobile scan application 130. Mobile scan application 130 may then use the URL returned by the destination server to send the media up to the destination server.

After the user has received and reviewed the data in the patient entry view 600, mobile scan application 130 may proceed to a media acquisition mode. In another example embodiment, the user may manually choose to proceed to the media acquisition mode by selecting a button in mobile scan application such as, for example, the Next button 610 in patient entry view 600 of FIGS. 6A and 6B. The media acquisition mode of mobile scan application 130 uses a camera in mobile imaging device 105 to capture media such as, for example, pictures and video clips (at block 225 of FIG. 2).

Figure 8:
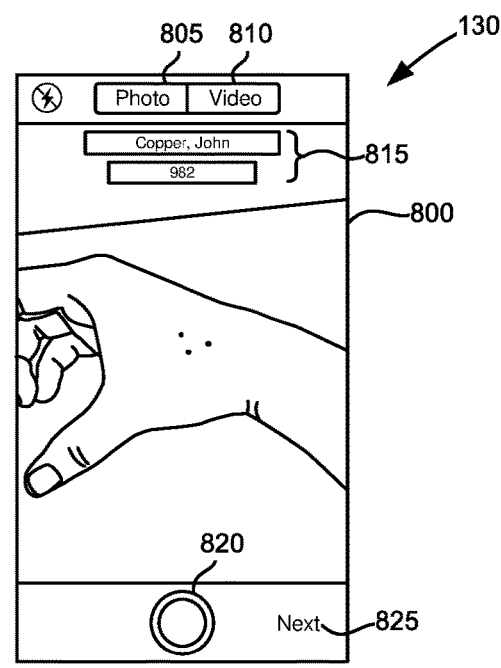
FIG. 8 shows an example media acquisition mode of mobile scan application.

FIG. 8 shows an example media acquisition mode 800 of mobile scan application 130. Media acquisition mode 800 allows the user to capture an image or a video using Photo 805 and Video 810 options that may be made available to the user. Information about the patient with which the media to be captured will be associated may be displayed in the media acquisition mode such as, for example, in a patient information display portion 815. It will be understood by those skilled in the art that other information about the patient or the study may be displayed in display portion 815. Multiple images or video clips may be captured using the capture button 820 for a single patient in the same session using media acquisition mode 800.

Once the media content has been captured, the captured content may be saved on a non-transitory computer readable storage medium of mobile imaging device 105. The user may indicate that the capturing is completed by selecting a button such as, for example, the Next button 825 in media acquisition mode 800.

Figure 9:
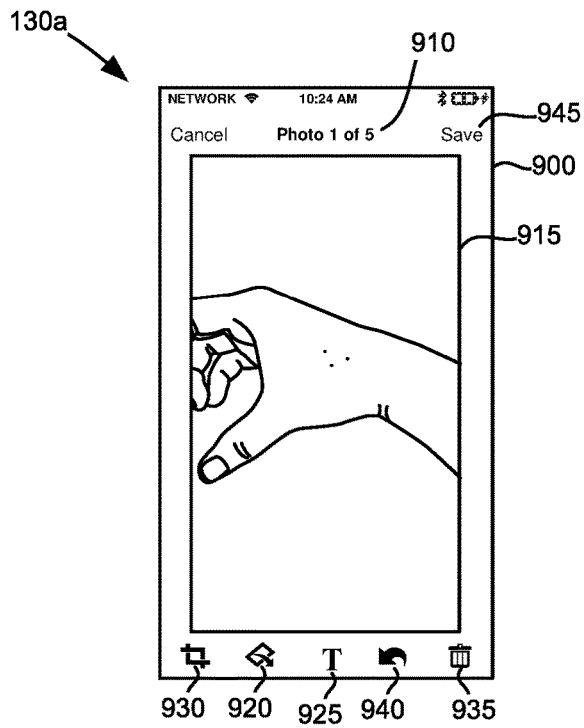
FIG. 9 shows an example interface of a media gallery showing one of the captured medical images for a particular patient.

Mobile scan application 130 may include a media gallery feature that allows the user to view the one or more captured content at block 230 in FIG. 2. FIG. 9 shows an example interface of a media gallery 900 showing one of the captured medical images for a particular patient. As shown in this example interface, media gallery 900 includes five photos for the specified patient as indicated in header 910. Media gallery 900 includes a display portion 915 that shows the captured content for the specified patient. The user may switch to another captured medical image by swiping the display portion 915 in a direction in order to view the other captured medical images.

In one example embodiment, a user may import to media gallery 900 photos and/or videos saved in an application of mobile imaging device 105 such as, for example, a camera roll or photo management application that organizes media that may have been captured at an earlier time or using another image-capturing application other than mobile scan application 130 installed in mobile imaging device 105. In this example embodiment, a user may select captured medical images and/or videos from the photo management application and import the captured medical images and/or videos to media gallery 900. In an alternative example embodiment, the user may import medical images and/or videos stored in a remote server to media gallery 900. The user may associate the imported medical images and/or videos with a specified patient. In another example embodiment, the medical images and/or videos may automatically be associated with the specified patient information upon being imported to media gallery 900. The user may select at least one of the imported medical images and videos as the captured media to be sent to the service.

Referring back to block 235 in FIG. 2, the captured media may be edited and/or deleted. Before sending to the service, the user may be allowed to edit the captured content. Editing may include rotating, cropping and annotating the captured content before sending it to the service. Media gallery 900 (shown in FIG. 9) may show editing options that may be performed on the one or more captured content. In one example embodiment, the user may rotate the captured images using a rotate button 920, add annotations to the images using annotation button 925, and/or crop the images using crop button 930 while in the gallery view. In another example embodiment, the user may delete images and/or video clips in the gallery view using the delete button 935. Media gallery 900 may also include an option to undo the changes made to the captured content using an undo button 940.

Figure 10:
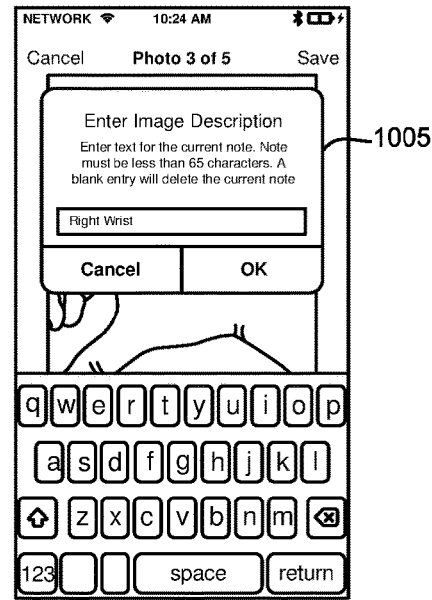
FIG. 10 shows an example interface for annotating the captured content.
Figure 11:
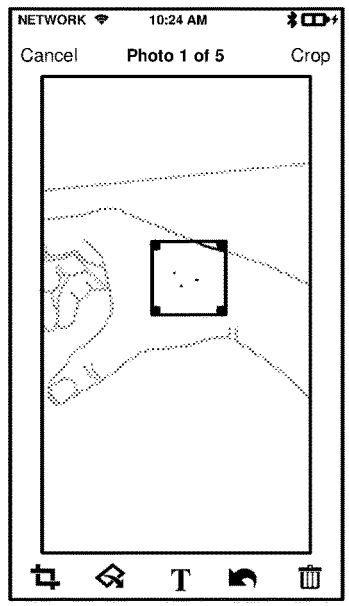
FIG. 11 shows an example interface for cropping the captured content.

FIG. 10 shows an example interface for annotating the captured content. Using annotation button 925, annotation interface 1005 may be displayed. Annotation interface allows the user to enter an image description for the captured content displayed in media gallery 900 of FIG. 9. FIG. 11 shows an example interface for cropping the captured content.

The user may then save the changes made to the captured content (using example save button 945 of FIG. 9) and send the captured content along with the patient demographics to core server 115 at block 240 of FIG. 2. The captured content may be associated with the patient demographics such as, for example, providing a metadata of the captured content that identifies the captured content as associated with the patient. The sending of the captured content along with the patient demographics may be sent over a secured channel using standard secure communication or transport protocols (e.g., HTTPS) such that the captured content and the patient demographics are encrypted in order to ensure integrity and security of the data being sent.

Figure 12:
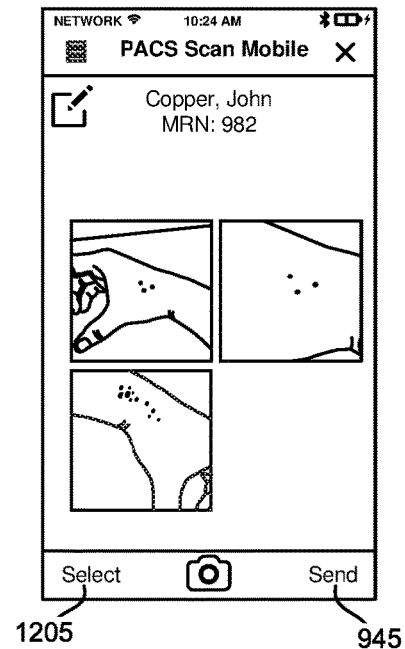
FIG. 12 shows an example media gallery that shows the captured medical images for a particular patient.

FIG. 12 shows an example media gallery that shows the captured medical images for a particular patient for sending to core server 115. The user may select which of the captured content to be sent using Select button 1205. In one example embodiment, the user may be asked for confirmation to send the captured content and patient demographics prior to the sending. In another example embodiment, mobile scan application 130 may display configured destination options to which the captured content and patient demographics will be sent. The configured destination options are specific servers that may be selected by the user as the destination where the captured content and patient data will be saved. The servers that the user may select may include servers for various formats of medical data such as, for example, HL7, DICOM, or XDS storage servers. In one example embodiment, when the user specifies that the destination is XDS, an XDS submission of the captured content may be created prior to transmitting the captured content to an XDS repository.

In continued reference to FIG. 2, at block 245, the captured media content and metadata may be received by core server 115. Core server 115 may receive the patient demographics with one or more image files and/or video clips, along with a choice of preconfigured DICOM destination. Core server 115 may process the received data and send or forward the patient metadata to the destination storage server specified by the user at block 250. Processing the received data may include translating the captured media content to a different format depending on the desired destination storage server. For example, processing the received data may include creating DICOM files based on the captured media content received from the mobile scan application, with the patient metadata included in the DICOM headers. Additionally, core server 115 may create one or more HL7 messages with information from the patient and/or study details and forward the one or more HL7 messages to at least one defined HL7 service. The created DICOM files may then be forwarded to the defined DICOM destination(s). In one example embodiment, HL7 messages may also be sent to one or more destinations in parallel.

At least one of the destinations that are communicatively connected with core server 115 may then receive the patient metadata and the captured content (at blocks 255a, 255b, and 255c). In one example embodiment, the destination server may be a DICOM storage server 125a that stores DICOM data, and the destination in this example embodiment may receive DICOM files with patient metadata in a DICOM header. Another example destination server may be an HL7 storage server 125b which may be a service that receives and stores HL7 messages. Still another example destination server may be an XDS server 125c that receives and stores XDS information. The destination servers may also be PACS destinations wherein submitted DICOM images may be received with correct patient metadata.

In one example embodiment, the destination servers 125a, 125b, 125c may confirm that the messages and data have been received. The confirmation may be sent to core server 115 and a notification may be displayed on an interface of mobile scan application 130 in mobile image device 105 to confirm the sending.

Mobile scan application 130 may also be used to manage jobs. Jobs may be a collection of information about a send operation that is created when a user sends data to a DICOM device via core server 115. The collection of information may include details such as, for example, who sent the data, when was the data sent, and from where. The information may also include a job status, which is a result of the send operation (whether or not the data has been successfully sent to the destination). The user may view a job history, or cancel or restart a failed job using the mobile scan application 130, or via the web console of core server 115.

It will be understood that the example applications described herein are illustrative and should not be considered limiting. It will be appreciated that the actions described and shown in the example flowcharts may be carried out or performed in any suitable order. It will also be appreciated that not all of the actions described in FIG. 2 need to be performed in accordance with the example embodiments of the disclosure and/or additional actions may be performed in accordance with other example embodiments of the disclosure.

Many modifications and other example embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of capturing medical imaging data for a patient using a mobile image-capturing device, comprising:
   accessing a function in an electronic health record application installed in the mobile image-capturing device that triggers the launch of an image management application installed in the mobile image-capturing device from the electronic health record application, the image management application separate from and integrated with the electronic health record application, wherein the electronic health record application passes each of (a) patient identifying information associated with the patient and (b) user-set configuration data to the image management application during the launch of the image management application from the electronic health record application, the user-set configuration data being specific to a user accessing the image management application and used to pre-configure the image management application;
   upon the user accessing the image management application, displaying at an interface of the image management application information regarding the patient based on the patient identifying information provided from the electronic health record application;
   importing to the image management application one or more medical images stored in the mobile image-capturing device;
   associating the one or more imported medical images with the patient identifying information; and
   transmitting the one or more imported medical images with the associated patient identifying information from the mobile image-capturing device to a storage location.

2. The method of claim 1, wherein the transmitting the one or more imported medical images with the associated patient identifying information from the mobile image-capturing device to a storage location is performed over a secured channel.

3. The method of claim 1, further comprising allowing a user to modify the information regarding the patient through the interface of the image management application.

4. The method of claim 1, further comprising receiving at the interface of the image management application a search query for use in searching for patient identifying information from an electronic health record storage server.

5. The method of claim 1, further comprising prior to transmitting the one or more imported medical images with the associated patient identifying information to the storage location, providing one or more storage server options for a user to select for where the one or more imported images and the associated patient identifying information will be transmitted.

6. The method of claim 1, further comprising prior to transmitting the one or more imported medical images with the associated patient identifying information to the storage location, editing the one or more imported images, the editing including at least one of rotating, cropping, and annotating the one or more imported images.

7. A mobile image-capturing device for capturing medical images for a patient, the mobile image-capturing device comprising:
   an imaging equipment accessible to a user of the mobile image-capturing device using a camera function of the mobile image-capturing device, the imaging equipment separate from and integrated with the image management application;

an electronic health record application installed in the mobile image-capturing device for use in accessing information of the patient; and an image management application installed in the mobile image-capturing device for managing one or more medical images for the patient, the image management application separate from and integrated with the electronic health record application, the imaging equipment separate from and integrated with the image management application, wherein the user launches the image management application from the electronic health record application by accessing a function in the electronic health record application that triggers the launch of the image management application from the electronic health record application, wherein upon the launching of the image management application, the image management application is provided with patient identifying information associated with the patient from the electronic health record application, wherein the image management application accesses the one or more medical images stored in the mobile image-capturing device, associates the one or more imported medical images with the patient identifying information, and transmits the one or more imported medical images with the associated patient identifying information from the mobile image-capturing device to a storage location, and wherein the image management application installed in the mobile image-capturing device is configured to allow editing of the associated patient identifying information in the image management application separately from the one or more medical images and to send the edited associated patient identifying information to a destination server.

8. The mobile image-capturing device of claim 7, wherein the electronic health record application accesses the information of the patient via an electronic health record server communicatively connected with the mobile image-capturing device.

9. The mobile image-capturing device of claim 7, wherein the image management application installed in the mobile image-capturing device is configured to allow editing of the one or more medical images separately from the editing of the associated patient identifying information, the editing of the one or more medical images including at least one of rotating, cropping, and annotating the one or more medical images.

10. The mobile image-capturing device of claim 7, wherein the user launches the image management application from the electronic health record application by accessing a link containing a uniform resource locator (URL) that triggers the launch of the image management application from the electronic health record application.

11. The mobile image-capturing device of claim 10, wherein the image management application is provided with the patient identifying information associated with the patient from the electronic health record application by passing the patient identifying information as a parameter of the URL used to trigger the launch of the image management application from the electronic health record application.

12. The mobile image-capturing device of claim 10, wherein the electronic health record application passes authentication information to the image management application as a parameter of the URL used to trigger the launch of the image management application from the electronic health record application, the authentication information used by the image management application to authenticate the user prior to giving the user access to the image management application.

13. The mobile image-capturing device of claim 7, wherein the electronic health record application passes each of (a) the patient identifying information associated with the patient and (b) user-set configuration data to the image management application during the launch of the image management application from the electronic health record application, the user-set configuration data being specific to a user accessing the image management application and used to pre-configure the image management application.

14. The method of claim 1, further comprising prior to transmitting the one or more imported medical images with the associated patient identifying information to the storage location:
    editing the associated patient identifying information in the image management application separately from the one or more imported medical images; and
    sending the edited associated patient identifying information to a destination server.

15. The method of claim 1, wherein the user-set configuration data is used in configuring at least one of (a) how an interface of the image management application is displayed and (b) a specific context with which the image management application is to be launched from the electronic health record application.

16. The mobile image-capturing device of claim 13, wherein the user-set configuration data is used in configuring at least one of (a) how an interface of the image management application is displayed and (b) a specific context with which the image management application is to be launched from the electronic health record application.

* * * * *